(12) United States Patent
Saracen et al.

(10) Patent No.: US 7,593,505 B2
(45) Date of Patent: *Sep. 22, 2009

(54) METHOD FOR AUTOMATIC ANATOMY-SPECIFIC TREATMENT PLANNING PROTOCOLS BASED ON HISTORICAL INTEGRATION OF PREVIOUSLY ACCEPTED PLANS

(75) Inventors: Michael J. Saracen, Oakland, CA (US); Jay B. West, Mountain View, CA (US)

(73) Assignee: Accuray Incorporated, Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/074,246

(22) Filed: Feb. 29, 2008

(65) Prior Publication Data

US 2008/0152085 A1 Jun. 26, 2008

Related U.S. Application Data

(63) Continuation of application No. 11/168,613, filed on Jun. 27, 2005, now Pat. No. 7,362,848.

(51) Int. Cl.
*A61N 5/10* (2006.01)

(52) U.S. Cl. ............................. 378/65; 378/64

(58) Field of Classification Search .................. 378/64, 378/65; 604/20
See application file for complete search history.

(56) References Cited

U.S. PATENT DOCUMENTS

| | | | |
|---|---|---|---|
| 6,385,286 B1 | 5/2002 | Fitchard et al. | |
| 6,560,311 B1 | 5/2003 | Shepard et al. | |
| 7,046,762 B2 * | 5/2006 | Lee | 378/65 |
| 7,066,883 B2 | 6/2006 | Schmidt et al. | |
| 7,266,176 B2 | 9/2007 | Allison et al. | |
| 7,362,848 B2 * | 4/2008 | Saracen et al. | 378/65 |
| 7,391,026 B2 * | 6/2008 | Trinkaus et al. | 250/363.02 |
| 2003/0208108 A1 | 11/2003 | Shewmake et al. | |
| 2007/0195930 A1 | 8/2007 | Kapatoes et al. | |

OTHER PUBLICATIONS

PCT International Search Report, PCT/US06/24923 filed Jun. 26, 2006, mailed Feb. 12, 2008.
PCT Written Opinion of the International Searching Authority, PCT/US06/24923 filed Jun. 26, 2006, mailed Feb. 12, 2008.
International Preliminary Report on Patentability, PCT/US2006/024923 filed Jun. 26, 2006, mailed Mar. 20, 2008.

* cited by examiner

*Primary Examiner*—Jurie Yun
(74) *Attorney, Agent, or Firm*—Blakely, Sokoloff, Taylor & Zafman LLP

(57) ABSTRACT

A method of automatically optimizing an inverse treatment plan by referencing data from an accepted plan library.

19 Claims, 16 Drawing Sheets

METHOD FOR AUTOMATIC ANATOMY-SPECIFIC TREATMENT PLANNING PROTOCOLS BASED ON HISTORICAL INTEGRATION OF PREVIOUSLY ACCEPTED PLANS

REFERENCE TO RELATED APPLICATIONS

This application is a continuation of application Ser. No. 11/168,613, filed Jun. 27, 2005, now U.S. Pat. No. 7,362,848 which is hereby incorporated by reference.

TECHNICAL FIELD

This invention relates to the field of radiation treatment, and in particular, to inverse planning in radiation treatment.

BACKGROUND

Tumors and lesions are types of pathological anatomies characterized by abnormal growth of tissue resulting from the uncontrolled, progressive multiplication of cells, while serving no physiological function.

A non-invasive method for pathological anatomy treatment is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source is changed, every beam passes through the tumor site, but passes through a different area of healthy tissue on its way to the tumor. As a result, the cumulative radiation dose at the tumor is high and the average radiation dose to healthy tissue is low. The term radiotherapy refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted by the magnitude of the radiation.

Conventional isocentric radiosurgery systems (e.g., the Gamma Knife) use forward treatment planning. That is, a medical physicist determines the radiation dose to be applied to a tumor and then calculates how much radiation will be absorbed by critical structures and other healthy tissue. There is no independent control of the two dose levels, for a given number of beams, because the volumetric energy density at any given distance from the isocenter is a constant, no matter where the isocenter is located.

Inverse planning, in contrast to forward planning, allows the medical physicist to independently specify the minimum tumor dose and the maximum dose to other healthy tissues, and lets the treatment planning software select the direction, distance, and total number and energy of the beams. Conventional treatment planning software packages are designed to import 3-D images from a diagnostic imaging source, for example, computerized x-ray tomography (CT) scans. CT is able to provide an accurate three-dimensional model of a volume of interest (e.g., skull or other tumor bearing portion of the body) generated from a collection of CT slices and, thereby, the volume requiring treatment can be visualized in three dimensions.

During inverse planning, a volume of interest (VOI) is used to delineate structures to be targeted or avoided with respect to the administered radiation dose. That is, the radiation source is positioned in a sequence calculated to localize the radiation dose into a VOI that as closely as possible conforms to the tumor requiring treatment, while avoiding exposure of nearby healthy tissue. Once the target (e.g., tumor) VOI has been defined, and the critical and soft tissue volumes have been specified, the responsible radiation oncologist or medical physicist specifies the minimum radiation dose to the target VOI and the maximum dose to normal and critical healthy tissue. The software then produces the inverse treatment plan, relying on the positional capabilities of the radiation treatment system, to meet the min/max dose constraints of the treatment plan.

FIG. 1 is a conceptual illustration of a graphical output of a treatment planning software displaying a slice of a CT image. The CT image is of a human chest region as viewed from the feet of a patient lying on his or her back, and includes the right lung, the left lung, and the spine region. The right lung contains a pathological anatomy (e.g., tumor, lesion, etc.) region targeted for radiation treatment and the spine region contains a critical anatomy, the spinal cord (surrounded by the vertebral body), to be avoided by radiation because of the spinal cord's proximity to the pathological anatomy. The treatment planning software enables the generation of a critical region contour around the spinal cord, a target (i.e., pathological anatomy) region contour around the pathological anatomy, and a corresponding dose isocontour on the displayed CT slice. Conventionally, a user manually delineates points (e.g., some of the dots on the contour lines of FIG. 1) on the display that is used by the treatment planning software to generate the corresponding contours. While this may seem an easy task, such matching is difficult due the 3-dimensional nature and irregularities of the pathological and normal anatomies.

The two principal requirements for an effective radiation treatment system are homogeneity and conformality. Homogeneity is the uniformity of the radiation dose over the volume of the target (e.g., pathological anatomy such as a tumor, lesion, vascular malformation, etc.) characterized by a dose volume histogram (DVH). An ideal DVH for the pathological anatomy would be a rectangular function as illustrated in FIG. 2, where the dose is 100 percent of the prescribed dose over the volume of the pathological anatomy and zero elsewhere. A desirable DVH for a critical region would have the profile illustrated in FIG. 3, where the volume of the critical anatomical structures receives as little of the prescribed dose as possible.

Conformality is the degree to which the radiation dose matches (conforms) to the shape and extent of the target (e.g., tumor) in order to avoid damage to critical adjacent structures. More specifically, conformality is a measure of the amount of prescription (Rx) dose (amount of dose applied) within a target VOI. Conformality may be measured using a conformality index (CI)=total volume at >=Rx dose/target volume at >=Rx dose. Perfect conformality results in a CI=1. With conventional radiotherapy treatment, using treatment planning software, a clinician identifies a dose isocontour for a corresponding VOI for application of a treatment dose (e.g., 3000 cGy).

As discussed above, in current inverse planning systems, the user manually sets constraints (e.g., minimum and maximum dose to critical and target regions) before planning. Optimization constraints can be very patient-specific, so that using the same constraints on different patients may lead to grossly different planning results. Based on a set of constraints defined by the operator, the quality of the treatment plan can be characterized with a DVH. If the resulting DVH is acceptable, the operator can then decide to proceed with the set of constraints that generated the acceptable DVH. If not, the operator would go through a process of modifying one or more of the optimization constraints to generate an acceptable DVH. Over time, a set of acceptable treatment plans can be collected for the patient to be referenced for future treatment plan development. Similarly, a library of acceptable treatment plans can be formed for a pathological anatomy in a given anatomical region. For example, when going through the process of developing a treatment plan for a pathological anatomy in the lung, the operator can reference a library of DVHs from acceptable plans and attempt to modify the optimization constraints to better conform the current DVH to the DVHs from the library. However, this can be a tedious and time-consuming process because the operator has to modify one or more optimization constraints manually, determine what the resulting DVH looks like, and continue to repeat the modification process until the DVH has the acceptable profile.

BRIEF DESCRIPTION OF THE DRAWINGS

The present invention is illustrated by way of example, and not by way of limitation, in the figures of the accompanying drawings.

DETAILED DESCRIPTION

Figure 1:
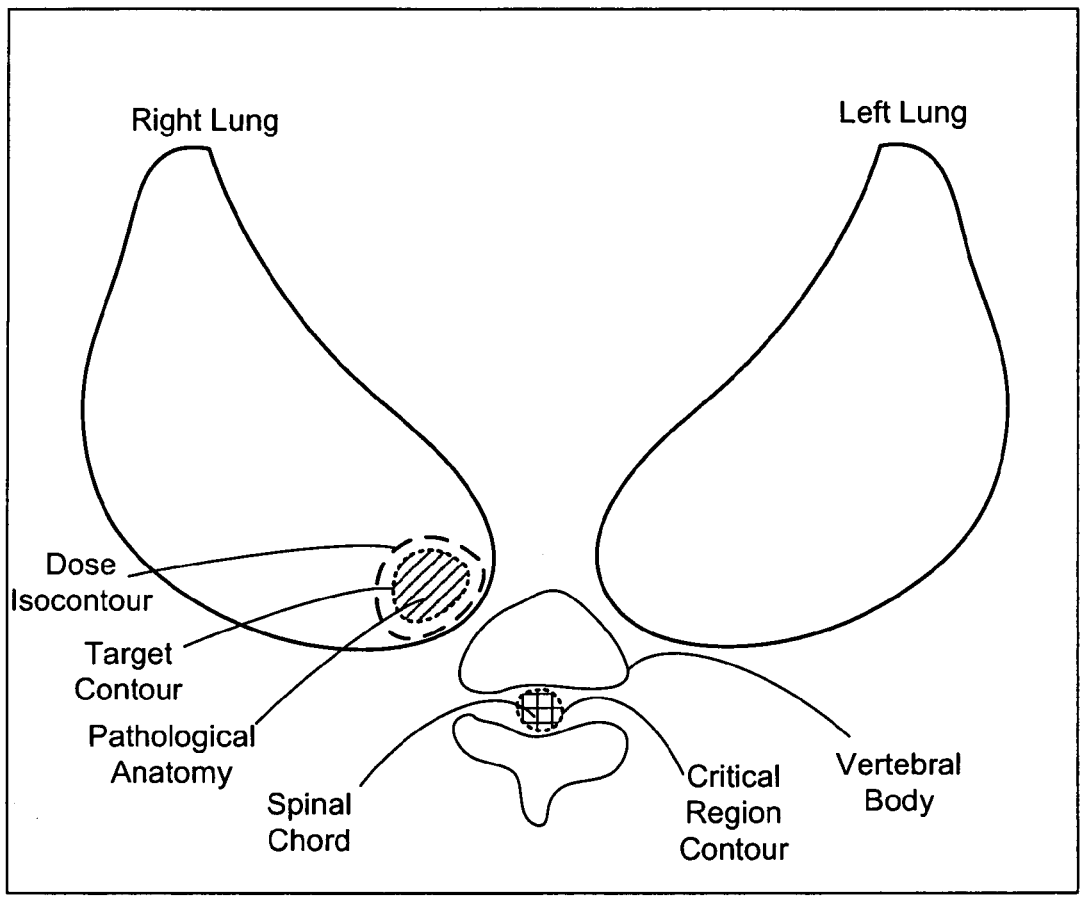
FIG. 1 illustrates a graphical output of a treatment planning software displaying a slice of a CT image.
Figure 2:
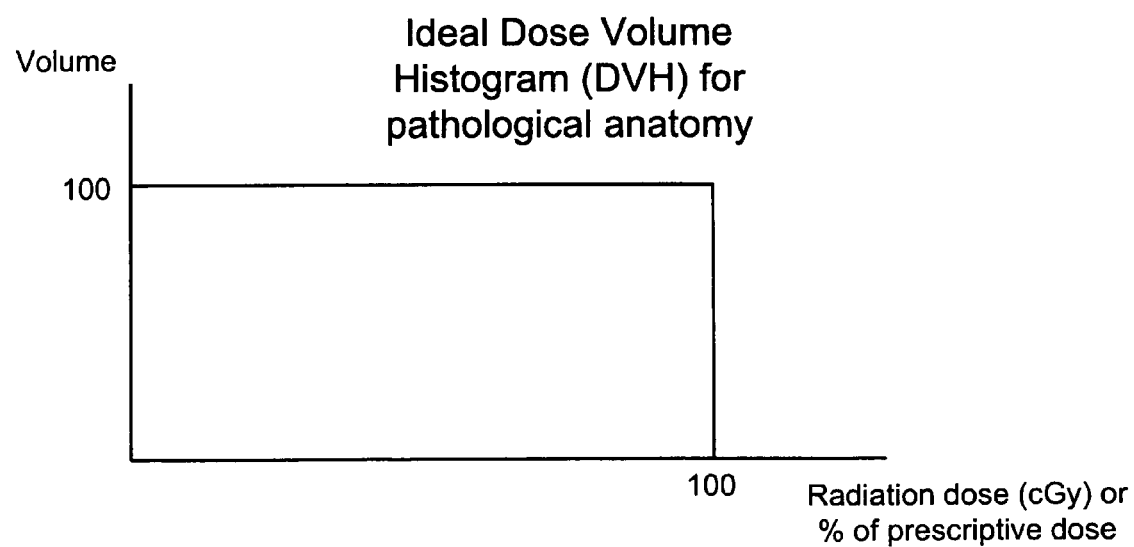
FIG. 2 is an ideal DVH for a pathological anatomy.

In the following description, numerous specific details are set forth such as examples of specific systems, components, methods, etc. in order to provide a thorough understanding of the present invention. It will be apparent, however, to one skilled in the art that these specific details need not be employed to practice the present invention. In other instances, well-known components or methods have not been described in detail in order to avoid unnecessarily obscuring the present invention.

Embodiments of the present invention include various steps, which will be described below. The steps of the present invention may be performed by hardware components or may be embodied in machine-executable instructions, which may be used to cause a general-purpose or special-purpose processor programmed with the instructions to perform the steps. Alternatively, the steps may be performed by a combination of hardware and software.

Embodiments of the present invention may be provided as a computer program product, or software, that may include a machine-readable medium having stored thereon instructions, which may be used to program a computer system (or other electronic devices) to perform a process. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or other type of medium suitable for storing electronic instructions.

Embodiments of the present invention may also be practiced in distributed computing environments where the machine-readable medium is stored on and/or executed by more than one computer system. In addition, the information transferred between computer systems may either be pulled or pushed across the communication medium connecting the computer systems, such as in a remote diagnosis or monitoring system. In remote diagnosis or monitoring, a user may utilize embodiments of the present invention to diagnose or monitor a patient despite the existence of a physical separation between the user and the patient. In addition, the treatment delivery system may be remote from the treatment planning system.

Embodiments of a treatment planning process are described that automatically derive optimization constraints within an inverse planning framework. In current inverse planning systems, the user sets constraints before planning (e.g., minimum and maximum dose to critical and target regions), either manually or by reading from a collection of preset constraints relevant to the anatomy being treated. In one embodiment of the present invention, the treatment planning software has access to one or libraries of accepted treatment plans that have been established over time for a given anatomy or VOI. For example, the plan library may be represented by a collection of acceptable DVHs for pathological anatomies in a given anatomical region. In addition to user manipulated optimization constraints, the treatment planning optimizer (e.g., software) may have the option of referencing the plan library to determine the conditions for an acceptable plan. Accordingly, the treatment planning optimizer automatically modifies one or more of the optimization constraints so that the planning result is guided towards one or more treatment plans in the plan library. In addition to using DVH as a planning result guide, other types of planning results may be used, such as homogeneity, conformality, and maximum dose.

Figure 4:
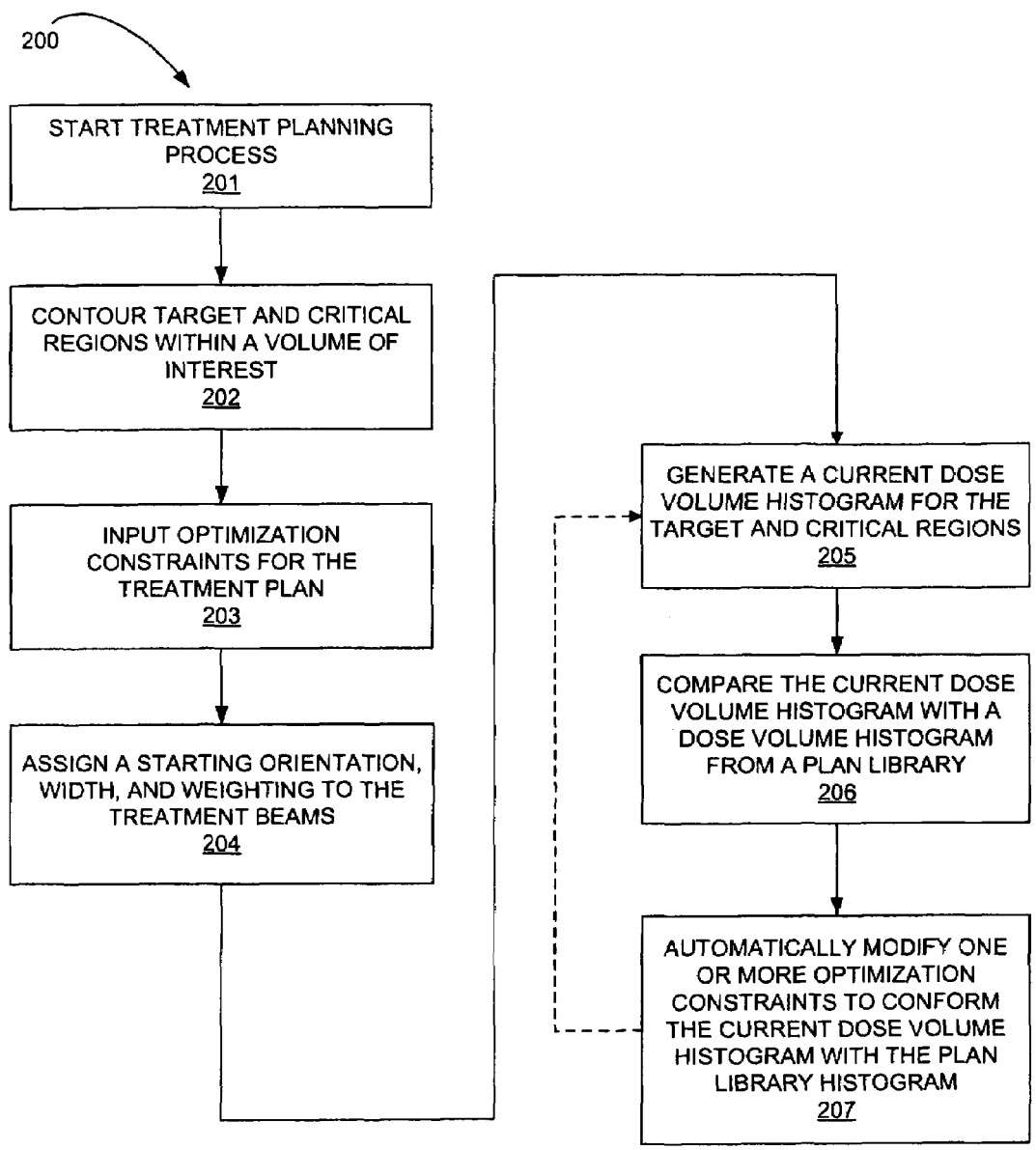
FIG. 4 is a flowchart generally describing one method of inverse planning using data from a library of acceptable plans to optimize a treatment plan.

FIG. 4 is a flowchart 200 generally describing one method of inverse planning using data from a library of acceptable plans to optimize a treatment plan. In one embodiment, the treatment planning process begins, at step 201, with receiving an anatomical image of the VOI targeted for radiation treatment. The anatomical image provides structural representations of the VOI containing the pathological anatomy (e.g., lesion) targeted for treatment, as well as surrounding tissue. For example, in one embodiment, the anatomical image can be a CT image slice. In examining the anatomical image on a display screen, the operator can identify the target region (e.g., pathological anatomy, lesion, tumor) for radiation treatment, and the presence of any critical regions near the target region for consideration so that the critical regions receive as little radiation as possible. In step 202, the operator delineates the target and critical regions by contouring these regions on the display screen. This involves drawing a visible line or a series of dots around the target and critical regions.

The operator can now input a parameter for one or more optimization constraints to maximize at least one of conformality and homogeneity, step 203. One type of optimization constraint is a minimum dose value for the target region and a maximum dose value for the critical region. Another type of optimization constraint relates to the radiation beams used in the treatment, such as radiation beam weight. As discussed in greater detail below with respect to FIG. 6, the beam weight (i.e., the total amount of radiation exiting a collimator for one beam or the amount of time a radiation beam is active) can be modified for the treatment plan. The beam weight can be set to a default or start value during the initial stages of the optimization process, step 204. Other types of radiation beam parameters include starting orientation and width. Steps 202-204 can be repeated for additional CT slices of the VOI so that a treatment plan that reflects an accurate picture of the pathological anatomy and/or critical regions can be developed. In one embodiment, a constraint may be defined as an input to an optimization routine (e.g., dose constraints specifying minimum and maximum dose to regions, beam constraints specifying the maximum weight allowed for a single beam). A parameter may be defined as a piece of information used to describe a particular treatment plan (e.g., beam orientations, sized, weights). After the optimization constraints have been received, and an initial beam weighting has been generated, the treatment planning software generates a set of dose isocontours, and a current DVH for the target and critical regions, step 205. As used herein, "current DVH" refers to the DVH for the treatment plan to be optimized. Ideally, the DVH for the target region is rectangular, where the dose is 100 percent of the prescribed dose over the volume of the pathological anatomy and zero elsewhere. For the critical region, a desirable DVH profile would show the critical anatomical structures receives as little of the prescribed dose as possible.

At this point, the treatment planning software can take advantage of data from previously accepted plans to optimize the treatment plan further. In one embodiment, the treatment planning software can access a database of accepted (i.e. successful) treatment plans for a given anatomy. The database of accepted treatment plans may be a collection of treatment plans that have been developed from different operators or treatment centers, and may reflect treatment plans from one patient or multiple patients. In one embodiment, the database may be a library of accepted plans characterized by DVHs for a given anatomy, for example, DVHs for the treatment of pathological anatomies in the prostate. The treatment planning software may be linked to any number of different libraries, and the libraries may be categorized according to anatomical region, organ, or critical region of interest. The libraries may also include a collection of different planning results other than target DVH, such as conformality, maximum dose, and dose volume coverage of critical regions.

One type of useful data that can be obtained from a DVH library, for example, is consistency of the DVH profile from the stored, accepted plans. If the accepted plans can be characterized with little or no deviations in their profiles, this pattern suggests to the plan operator that the current DVH should have a profile similar to the DVH profiles from the plan library. However, if the DVH profiles from the plan library vary widely or show no consistency, this may suggest to the plan operator that the DVH profile is not an important factor in the treatment plan optimization process. In one embodiment, whether previous accepted treatment plans generate consistent DVH profiles may be influenced by the size of the pathological anatomy or the location of the pathological anatomy with respect to the surrounding anatomy or critical structures. For example, an accepted plan library for the treatment of a pathological anatomy within the prostate may have a consistent DVH profile whereas an accepted plan library for the treatment of a pathological anatomy within the lung may have an inconsistent profile. Because the prostate is a relatively small organ compared to the lung, a significant portion of the prostate, as well as surrounding critical structures such as the rectum, may be exposed to radiation during treatment. As such, a history of accepted plans may show consistent DVH profiles for the target region and/or critical region. In the lung, the DVH may be greatly influenced by the location of the pathological anatomy. For example, a pathological anatomy located near a critical structure such as the spinal cord may produce a significantly different acceptable plan relative to a treatment for a pathological anatomy located closer to the chest wall and away from the spinal cord.

Given the potential advantage of referencing data from accepted plan libraries, the current DVH, for example, can be compared to an accepted plan library for the same anatomical region, step 206. If the treatment plan involves a pathological anatomy located within the prostate, the current DVH can be compared to a library of accepted DVHs for prostate treatment plans. In one embodiment, the comparison of the current DVH to the accepted plan DVH may first involve determining whether there is a consistency in the DVH profiles in the plan library. If so, the treatment planning software automatically modifies one or more optimization constraints to conform the current DVH with the pattern of DVHs in the plan library, step 207. In one embodiment, one of the parameters that can be modified as a consequence of changing optimization constraints is beam weight. For the target region, the amount of radiation delivered by each beam can be determined by defining a beam width and the total time the beam is active when directed toward the target region. By either altering the beam width or delivery time, the beam weight can be controlled, which ultimately influences the amount of radiation dose to the target region. Changing even one beam weight can influence the DVH profile for either the target region or the critical region. The treatment planning software, in one embodiment, automatically modifies one or more beam weights to conform the current DVH profile to a DVH profile from the accepted plan library, when appropriate. In one embodiment, various steps of process 200 is iterative, and in particular, steps 205 through 207 can be repeated as often as necessary until a desirable current DVH profile is obtained. After one or more treatment constraints have been optimized as reflected in a desirable DVH, the operator may save the treatment plan for later use and/or add the treatment plan to a particular library of accepted treatment plans for use by other operators as part of a treatment plan optimization process.

Figure 5:
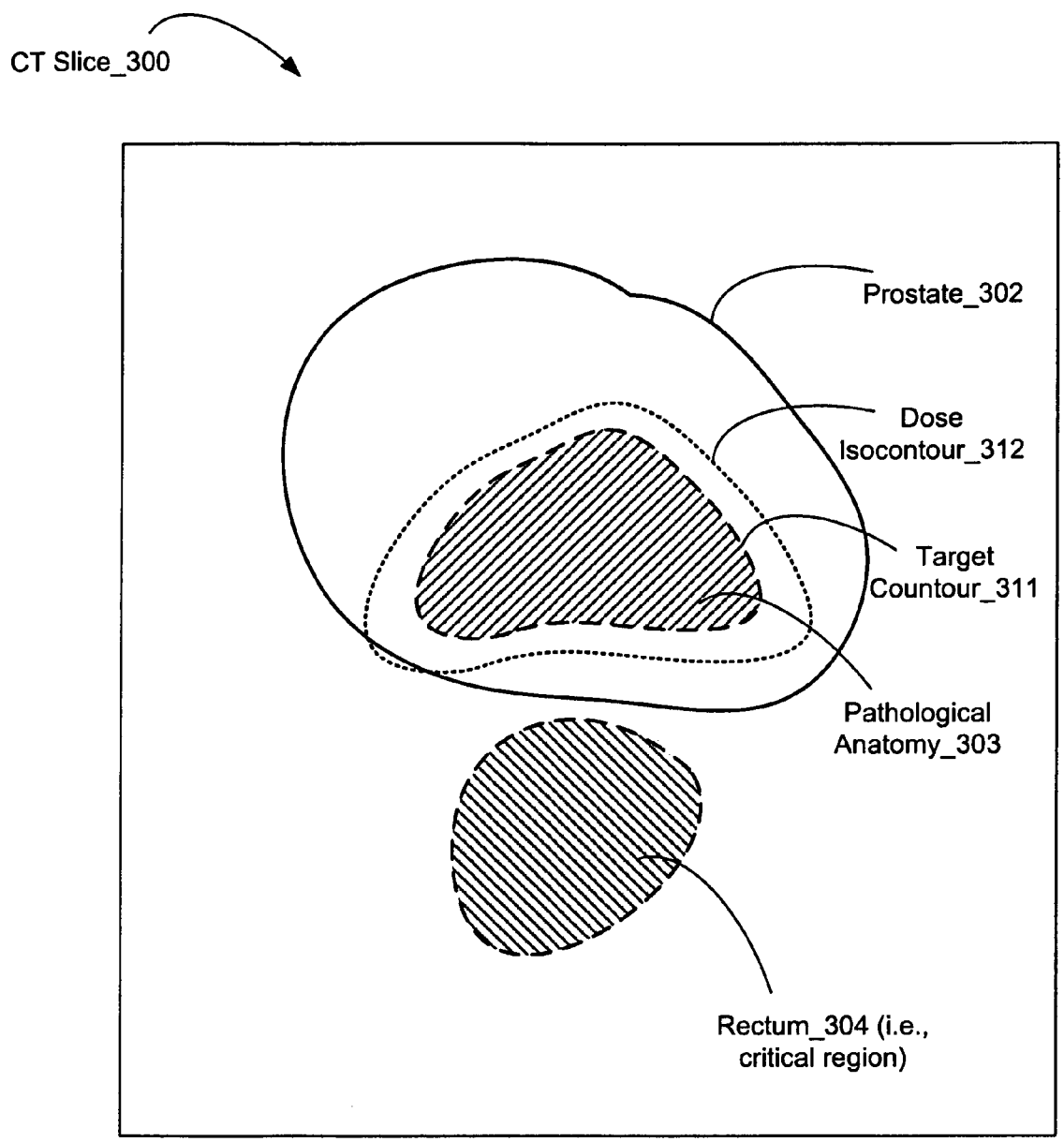
FIG. 5 illustrates a VOI represented by a CT slice including the prostate and rectum.

FIGS. 5-9 illustrate, in greater detail, one embodiment of a process to optimize a radiosurgery treatment plan for a pathological anatomy within a specific anatomical region. FIG. 5 illustrates VOI represented by a CT slice 300 of prostate 302 and rectum 304. Pathological anatomy 303 is shown having a substantial size relative to the size of prostate 302 in slice 300. For clarity of description, other anatomical structures proximal to prostate 302 and rectum 304 have been omitted. As part of inverse planning, a target contour 311 (represented as a segmented border) is drawn around pathological anatomy 303 to delineate a target region. A contour is also drawn around rectum 304 to delineate a critical region. In one embodiment, the contours of FIG. 5 may be generated using inverse planning in which dose constraints such as the minimum dose for the pathological anatomy 303 (i.e., the target region) and the maximum dose to rectum 304 (i.e., the critical region) are specified by a user. Based on the specified dose constraints, the treatment planning software selects the direction, distance, and total number and energy of the beams that is used to implement the treatment plan. A radiation source is positioned in a sequence calculated to localize the radiation dose into the VOI shown in CT slice 300 that as closely as possible conforms to pathological anatomy 303, while avoiding exposure to rectum 304. The treatment planning software then produces an inverse treatment plan, relying on the positional capabilities of the radiation treatment system, to meet dose constraints as closely as possible.

The dose isocontour 312 may be generated by the treatment software, using as input the current position, size, and weighting of the treatment beams. Ideally, the dose isocontour 312, as well as for the other slices in the VOI, should exactly match target contour 311 target over its 3-dimensional volume. The generation of a dose isocontour is known in the art; accordingly a more detailed description is not provided.

The treatment planning software also performs a radiation dose calculation for the VOI displayed in CT slice 300. The treatment planning software considers a set of beams that are directed at pathological anatomy 303. In one embodiment, the treatment planning software is used with a radiation source that has a collimator that defines the width of the set of beams that is produced and determines, for example, the number of beams, their sizes (e.g., as established by the collimator), their positions and orientations, as well as the amount of radiation from each beam. The total amount of radiation exiting the collimator for one beam is defined in terms of Monitor Units (MU). Because the intensity of the radiation source is constant, the MU is linearly related to the amount of time for which the beam is enabled. The radiation dose absorbed due to a given beam (in units of cGy) by tissue in the path of the beam is also linearly related to the MU. The absorbed dose related to a beam is also affected by the collimated size of the beam, the amount of material between the collimator and the calculation point, the distance of the collimator from the calculation point, and the distance of the calculation point from the central axis of the beam.

Figure 6:
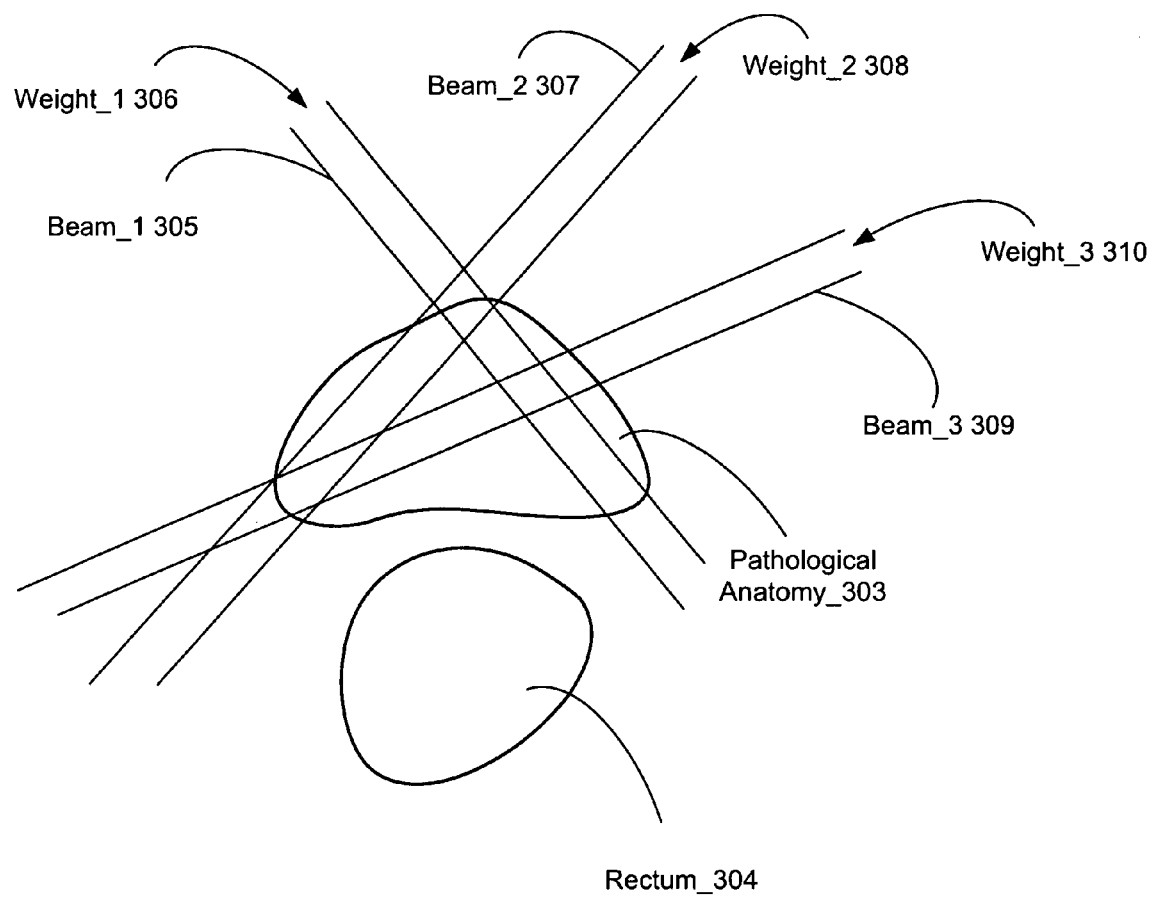
FIG. 6 illustrates a 2-dimensional perspective of radiation beams originating from a radiation treatment system directed at a pathological anatomy.

FIG. 6 illustrates a 2-dimensional perspective of radiation beams originating from a radiation treatment system directed at pathological anatomy 303. It should be noted that 3 beams, beam_1 305, beam_2 307, and beam_3 309, are illustrated in FIG. 6 only for ease of discussion and that an actual treatment plan may include more, or fewer, than 3 beams. Moreover, the 3 beams are representative of conformal planning, in which each beam terminates at various points within pathological anatomy 303. In conformal planning, some beams may or may not intersect or converge at a common point, and although the 3 beams appear to intersect in the 2-dimensional perspective of FIG. 6, the beams may not intersect in their actual 3-dimensional space. The radiation beams need only intersect with the target volume and do not necessarily converge on a single point, or isocenter, within the target. The 3 beams may initially have substantially similar beam weights, as represented by weight_1 306, weight_2 308, and weight_3 310. The initial beam weights may be a default beam weight determined by the operator or the treatment planning software. The initial beam weights may also be influenced by the prescribed radiation dose to be delivered to pathological anatomy 303. For example, if a total prescribed dose of 3500 cGy is set for pathological anatomy 303, the treatment planning software would automatically determine the beam weights for each beam to balance conformality and homogeneity to achieve that prescribed dose as close as possible.

Figure 3:
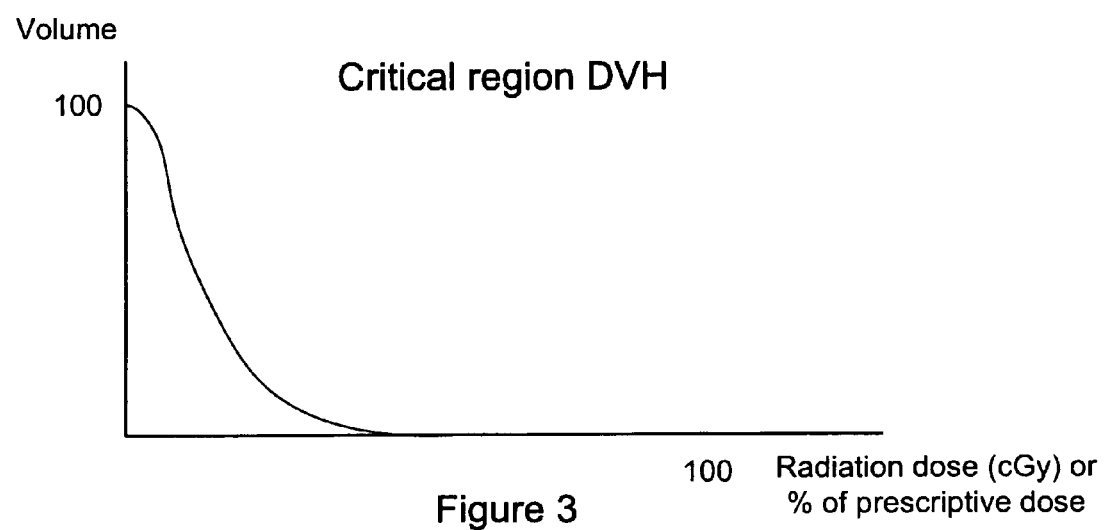
FIG. 3 is a desirable DVH for a critical region.
Figure 7:
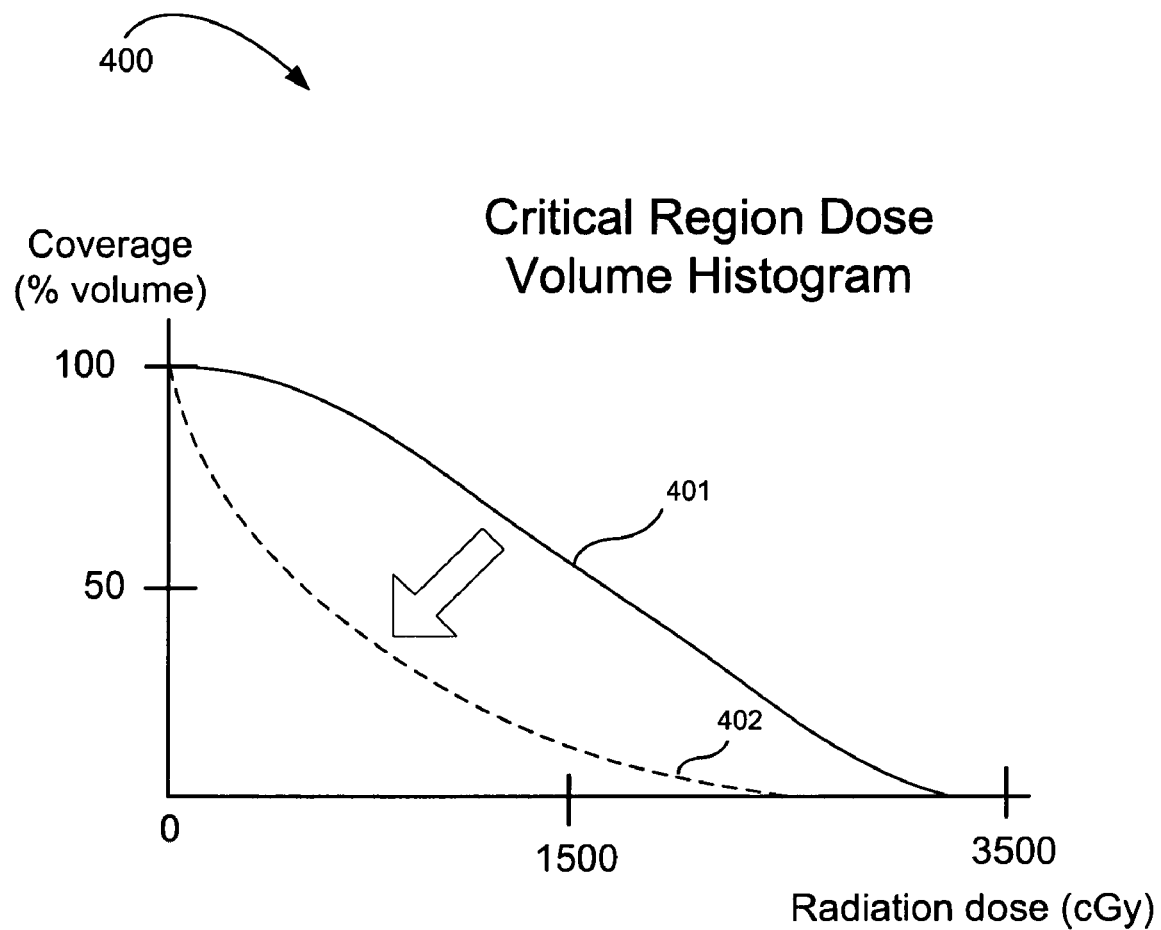
FIG. 7 illustrates a current DVH for a critical region based on the initial set of treatment plan constraints.

Based on the initial set of treatment constraints for pathological anatomy 303, a DVH can be generated to view the results of the proposed treatment plan in terms of the volume of pathological anatomy 303 that receives the prescribed dose. Similarly, a DVH can be generated to view the treatment plan results for rectum 304 (i.e., the critical region). FIG. 7 illustrates a current DVH 400 for rectum 304 based on the initial set of treatment plan constraints. Profile 401 indicates that the treatment results are far from ideal (as illustrated in FIG. 3), as about 50% of the rectum receives at least 1500 cGy, which corresponds to about 50% of the total dose. At first glance, the operator may believe that rectum 304 would receive a radiation dose greater than what is acceptable, suggesting that further optimization is necessary to produce a DVH profile where a greater percentage of rectum 304 receives less of the overall radiation dose.

Figure 8:
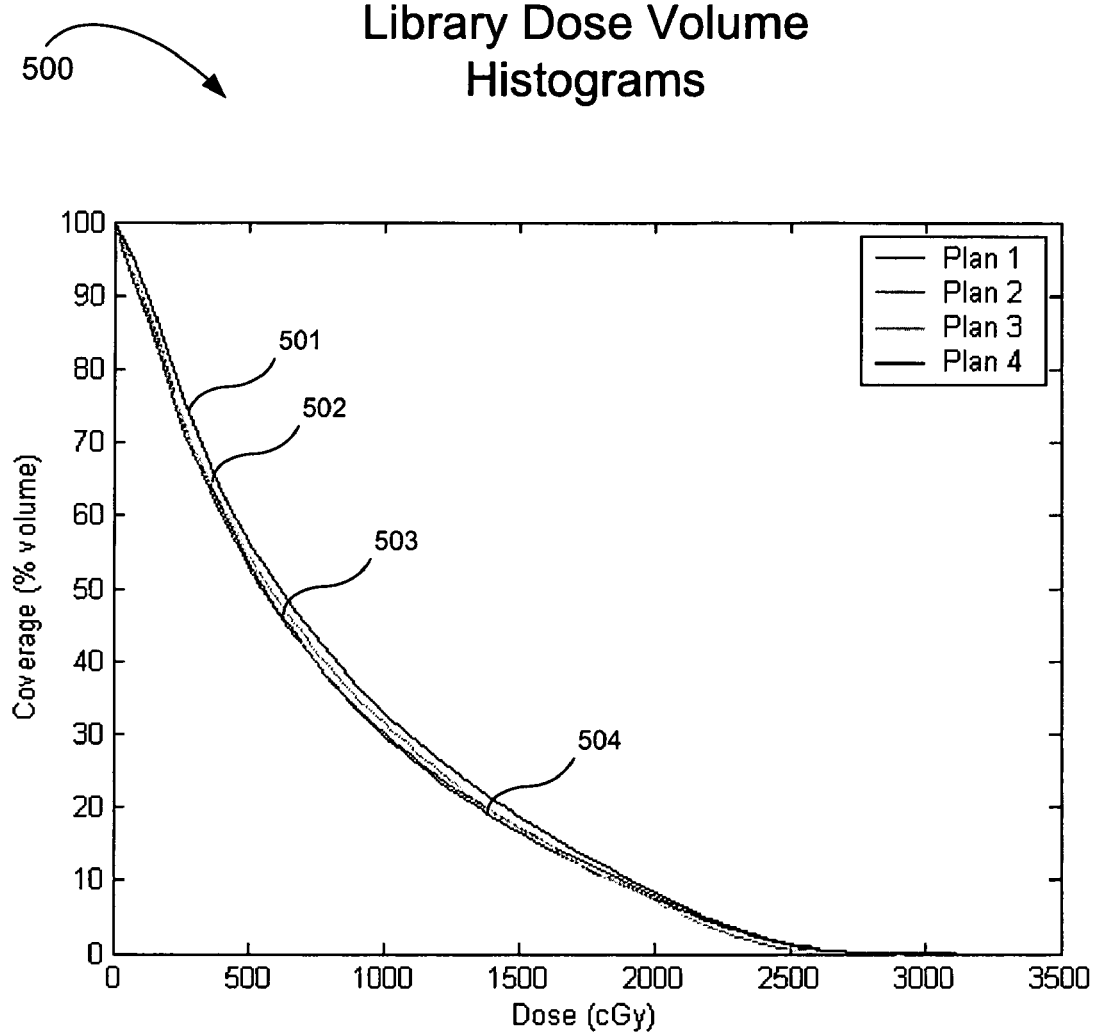
FIG. 8 illustrates a DVH including a library of profiles from previously accepted plans.
Figure 9:
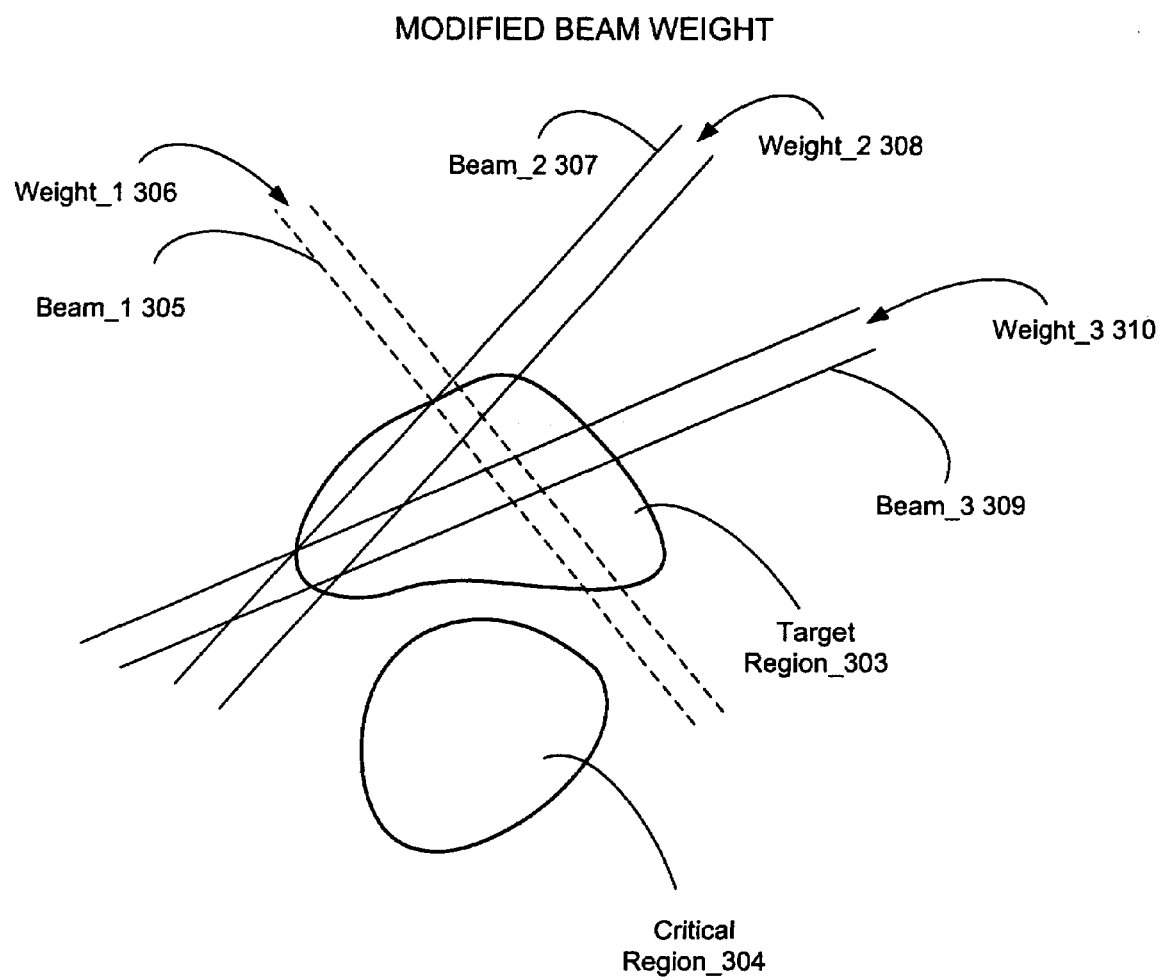
FIG. 9 representatively illustrates the changing of a beam weight.

In one embodiment, the treatment plan may be optimized further by referencing a library of accepted treatment plans for the prostate gland in which the rectum was identified as a critical structure. Accepted treatment plans refer to a set of beam weights, sizes, and positions that result in successfully balancing treatment of the pathological anatomy while minimizing radiation dose to critical structures. One format for characterizing accepted treatment plans is through their respective DVH profiles, for both the pathological anatomy and critical structures. In the example of rectum 304, the treatment planning software can search a database of accepted plans and determine whether a DVH library exists for VOIs including the prostate gland and the rectum. If such a library exists, the treatment planning software next determines whether there is any consistency to the DVH profiles. FIG. 8 illustrates a DVH 500 including a library of profiles from previously accepted plans, as represented by plan_1 501, plan_2 502, plan_3 503, and plan_4 504, for a rectum when treating a pathological anatomy within the prostate gland. The consistency of profiles 501-504 strongly suggests that it is important that the DVH of the rectum 304 reflect this particular pattern. Accordingly, one or more optimization constraints can be modified to conform profile 401 with profiles 501-504. In one embodiment, one or more radiation beams may be modified (e.g., their positions and/or widths changed, and/or their weights increased or decreased) automatically by the treatment planning software to change profile 401. FIG. 9 representatively illustrates the modification of beam_1 305 by changing a beam width (in this case the beam width is narrowed relative to the width shown in FIG. 6). With a change of one beam width, the treatment planning software generates another DVH and compares the new current DVH profile with profiles 501-504. This process can be repeated for each beam that is to be used for treatment until the best possible fit is made.

Figure 16:
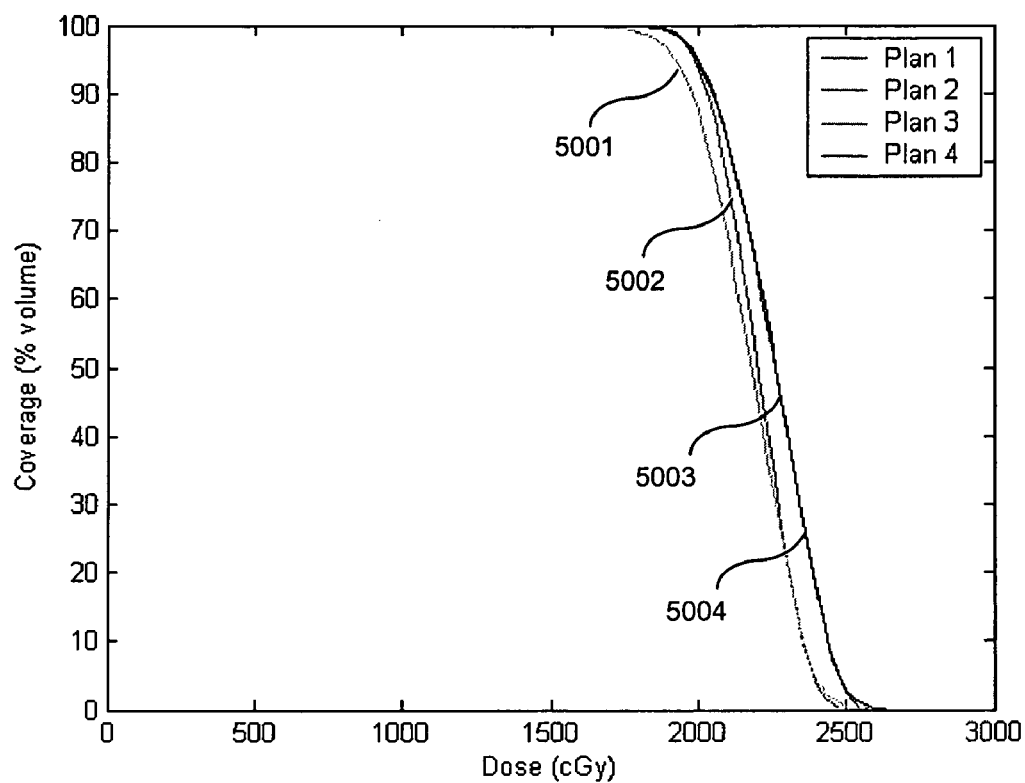
FIG. 16 illustrates a DVH including a library of profiles from previously accepted plans for a target region.
Figure 17:
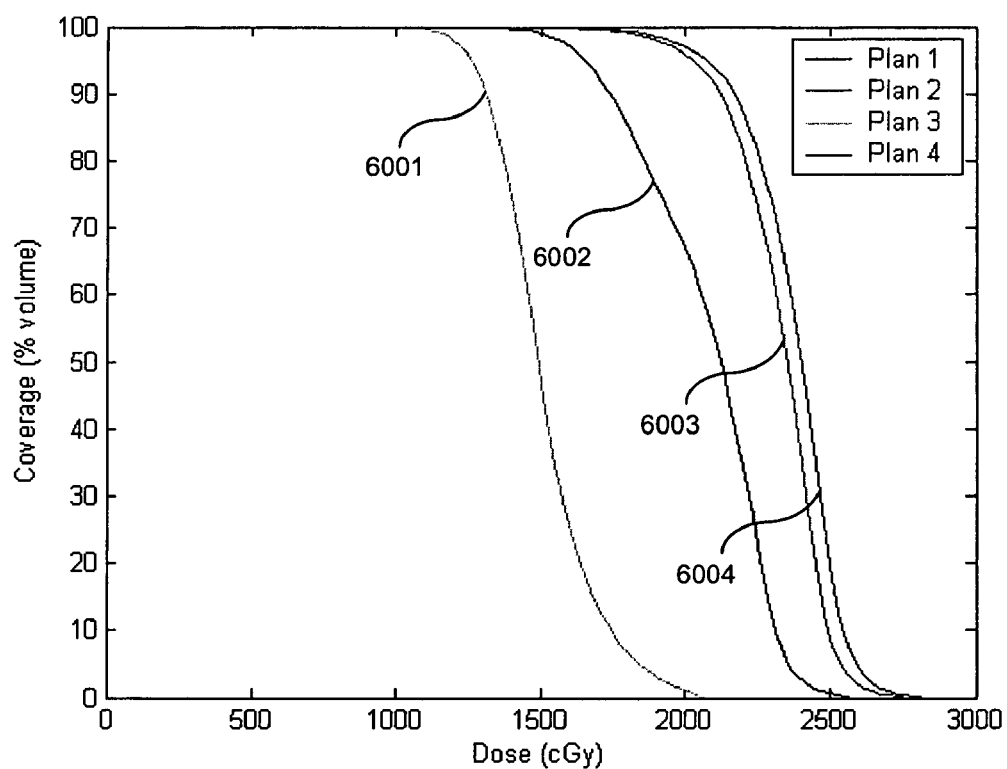
FIG. 17 illustrates another DVH including a library of profiles from previously accepted plans for a target region.

A treatment plan library for pathological anatomy 303 (i.e., the target region) can be referenced in a manner similar to rectum 304 for optimization. FIG. 16 illustrates DVH 5000 including plan_1 5001, plan_2 5002, plan_3 5003, and plan_4 5004 corresponding previous accepted plans for the prostate region. The consistency of the profiles in plans 1-4 may be used as a guide to conform a present DVH for the target region (not shown) by modifying one or more optimization constraints. Alternatively, as illustrated in DVH 6000 of FIG. 17, if the plan library does not exhibit consistent profiles for a target region in the prostate, the treatment planning software would not rely on DVH results as a treatment planning guide. The accepted plans (plan_1 6001, plan_2 6002, plan_3 6003, and plan_4 6004 of DVH 6000) vary widely in which 100% of the pathological anatomy volume receives between about 1500 cGy to about 2500 cGy. The large range of DVH values for accepted plans may suggest that DVH is not a significant factor in optimizing the treatment plan.

For target and critical structures (e.g., pathological anatomy 303 and rectum 304), the following algorithm may be used to optimize beam weights based on a comparison of the current DVH with DVHs from a library of accepted plans:

For all beams
   Set beam weight to start value W
End

For all targets and critical structures
   Read "perfect" DVH values D_p from plan library
End Do
   For all targets and critical structures
      Calculate current DVH values D_c from plan library
   End
   Set Delta=0.1* mean beam weight
   Set number of weights changed to zero
   For all Beams
      Calculate current deviation C(D_c)=sum ((D_c−D_p)*(D_c−D_p))
      Increment beam weight by Delta
      Calculate current DVH values D_c
      Calculate deviation C(D_c)(+)
      Decrement beam weight by Delta
      Decrement beam weight by Delta
      Calculate current DVH values D_c
      Calculate deviation C(D_c)(−)
      Increment beam weight by Delta
      If (C(D_c)(+)<C(D_c) and C(D_c)(+)<C(D_c)(−))
         Increment beam weight by Delta
         Increment number of weights changed
      Else if (C(D_c)(−)<C(D_c) and C(D_c)(−)<C(D_c)(+))
         Decrement beam weight by Delta
         Increment number of weights changed
      Else
         Leave beam weight as-is
      End
      Calculate current DVH values D_c
   End
   Calculate current deviation C(D_c)=sum((D_c−D_p)*(D_c−D_p)) While (C(D_c)>termination threshold or number of weights changed=0).

For ease of explanation, the above algorithm is described with respect to optimizing beam weights for the treatment results on rectum 304, although the process is performed for each target region and critical region. In one embodiment, the algorithm involves increasing and decreasing a beam weight for each beam, and determining the effect on the current DVH. The treatment planning software does not know what effect increasing or decreasing a beam weight has on the current DVH without actually calculating a result. Because the goal of the optimization process is to conform the current DVH as closely as possible to the DVH profile from the accepted plan library, a series of comparisons is performed before the treatment planning software determines whether a beam weight should be increased or decreased. The treatment planning software initially sets all the radiation beams weights to a starting value and an ideal or perfect DVH value from an accepted plan library is identified. In one embodiment, the ideal DVH value may be the mean value of all the DVH values from the accepted plan library (e.g., DVH values from DVH 500 of FIG. 8). Then, the current DVH for rectum 304 is calculated (e.g., as shown in DVH 400 of FIG. 7). An amount (i.e., Delta) by which the beam weight is changed incrementally is also established. For example, the Delta may be set at about 10% of the mean beam weight.

For all the beams to be used in the treatment plan, the treatment planning software calculates a current deviation between the ideal DVH value from the plan library and the current DVH value. Then, starting with the first beam (e.g., beam 1_305), its corresponding beam weight (e.g., beam weight 1_306) is increased by value Delta. A first, new current DVH value is calculated followed by measuring a first deviation of the first, new current DVH relative to the ideal DVH. This first deviation measurement is then stored. The beam weight is then reduced by value Delta to return the beam weight to its original value. The beam weight is again reduced by value Delta and a second, new current DVH value is calculated, followed by measuring a second deviation of the second, new current DVH with the ideal DVH. This second deviation measurement is then stored. The beam weight is then increased by value Delta to return it to its starting value. If the first deviation is greater than both the current deviation and the second deviation, the beam weight for the first beam is increased by value Delta. If the second deviation is less than both the current deviation and the first deviation, the beam weight for the first beam is decreased by value Delta. If either condition is satisfied, the counter of changed beam weights is also increased. If either condition is not satisfied, the beam weight is left unchanged. This process may be repeated until the current deviation is no longer greater than a termination threshold value or until the counter of beam weights changed is zero. Referring again to FIG. 7, the adjustment of one or more beam weights results in a DVH profile 402 that is consistent with the plan library DVHs of FIG. 8. The optimized current treatment plan (including the current DVH) may then be stored in a database for future reference and/or may be added to an accepted treatment plan library to be used in an optimization process in developing other treatment plans.

Figure 10:
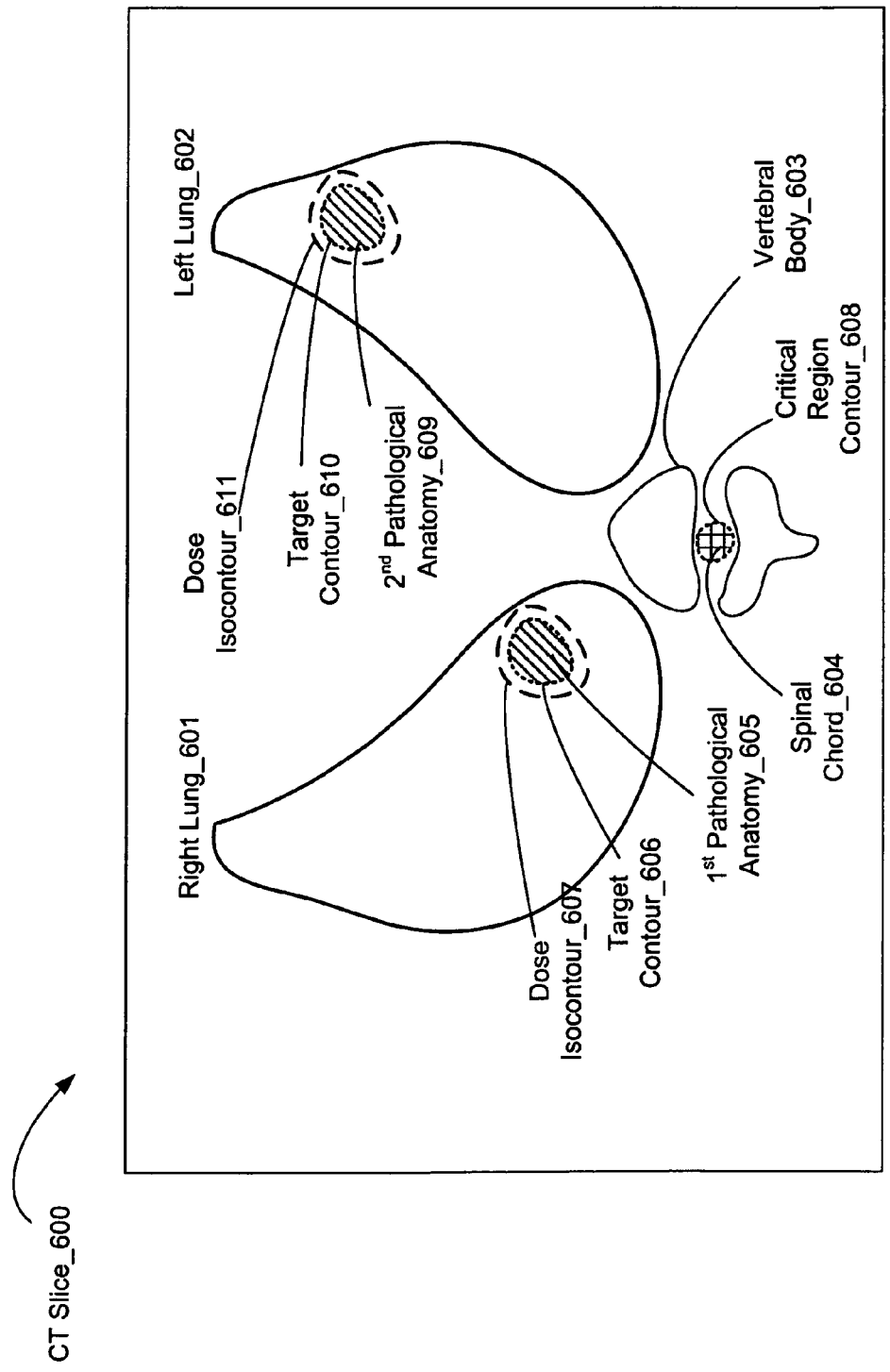
FIG. 10 is a graphical output from a treatment planning software displaying a slice of a CT image.
Figure 11:
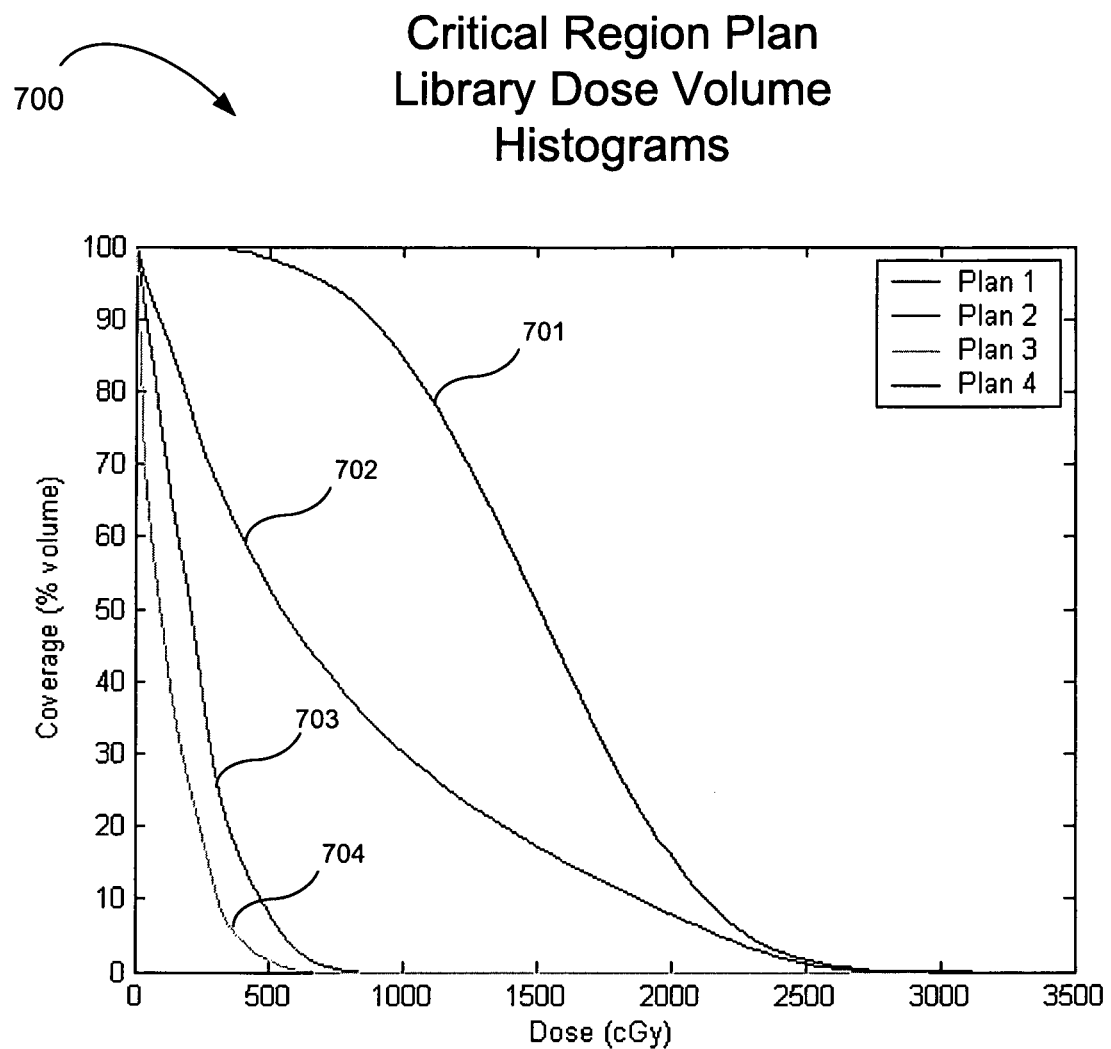
FIG. 11 illustrates another DVH including a library of profiles from previously accepted plans.

In one embodiment, the treatment planning software may not execute the optimization process described above if the accepted plan library does not exhibit consistent DVH profiles or has widely varying DVH values. A widely varying DVH library may suggest that modifying optimization constraints to force a particular DVH profile is not a factor for a successful treatment plan. FIGS. 10-11 illustrate an embodiment of a scenario in which data from an accepted plan library would not factor in the optimization for treatment planning.

FIG. 10 is a graphical output from a treatment planning software displaying a slice 600 of a CT image. The CT image is of a human chest region as viewed from the feet of a patient lying on his or her back, and includes right lung 601, left lung 602, vertebral body 603, and spinal cord 604. A first pathological anatomy 605 is found in right lung 601 identified by target contour 606 and a second pathological anatomy 609 is found in left lung 602 identified by target contour 610 (i.e., the target regions). Spinal cord 604 has also been identified by critical region contour 608. Dose isocontours 607 and 611 may be automatically generated at each iteration of the planning process.

After current DVHs are generated for the target and critical regions, the treatment planning software may reference an accepted plan library corresponding to previous treatments for the same anatomy (i.e., pathological anatomies in the lung anatomy with the spinal cord as a critical structure). For example, it may be appropriate that a current DVH for spinal cord 604 can be modified to fit the DVH profiles for the accepted plan library. FIG. 11 illustrates DVH 700 including plan_1 701, plan_2 702, plan_3 703, and plan_4 704. Even though the DVH profiles of plans 1-4 reflect accepted treatment plans, their lack of uniformity suggests that optimizing the current treatment plan based on plan library DVH values should not be considered. With respect to the algorithm described above, a threshold deviation value may be set for the DVH values within the plan library such that if a certain number of DVH values exceed the threshold value, no process is executed to fit the current DVH with an ideal DVH from the plan library. For example in one embodiment, a mean DVH value can be calculated from all the DVH values in the plan library, and each DVH value is compared against the mean value. If a certain number of DVH values deviate from the mean value by a defined threshold, no ideal DVH value is calculated and the data from the plan library is not used for treatment plan optimization.

Figure 12:
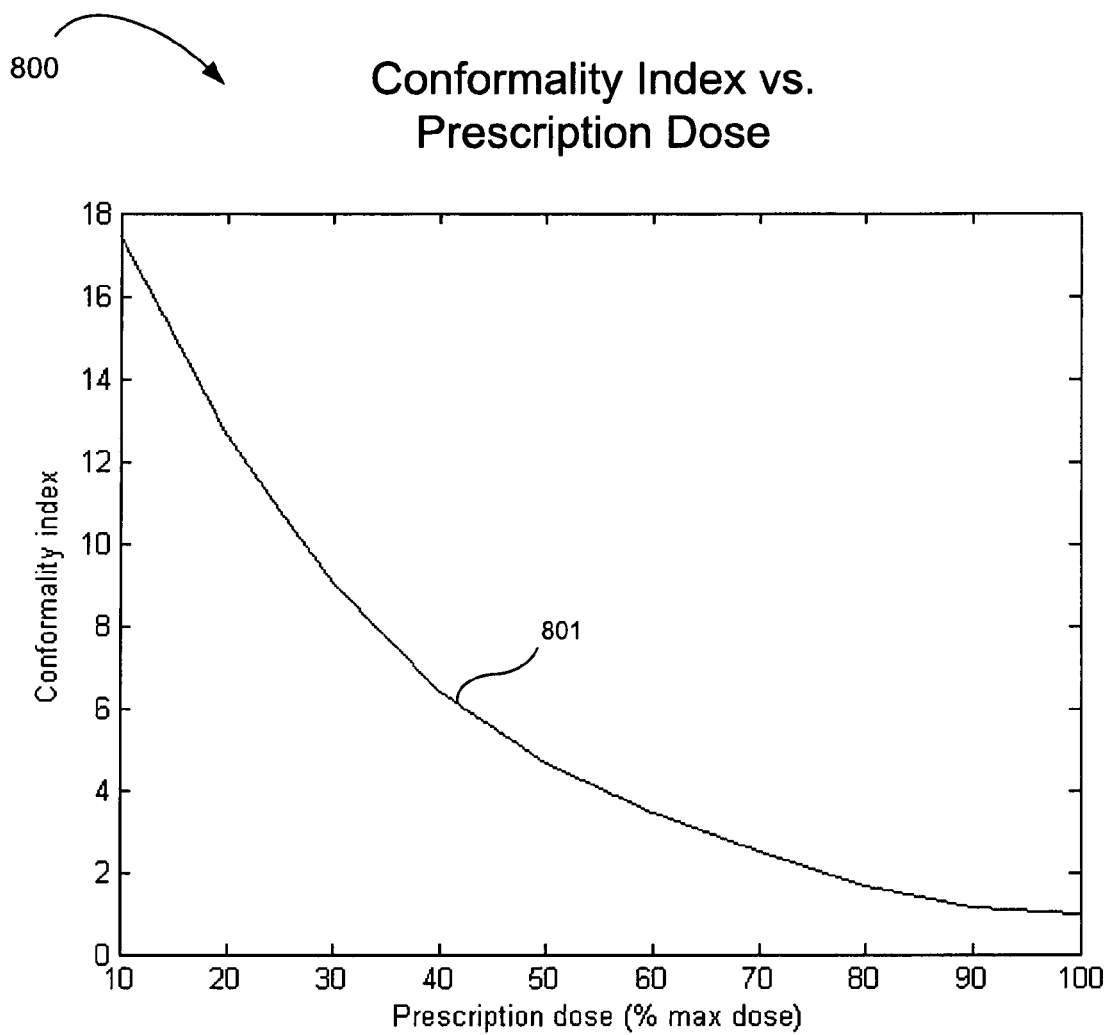
FIG. 12 illustrates an exemplary graph of conformality index vs. prescription dose.

Although the use of accepted plan libraries has been described with respect to DVH profiles and values, it may be appreciated that in alternative embodiments, other types of treatment planning results such as homogeneity, conformality, and maximum dose may be included as part of the library. Conformality may be expressed in terms of a conformality index (CI), which is the ratio of the tissue volume receiving the prescription dose or more, to the tumor volume receiving the prescription dose or more. FIG. 12 is an exemplary graph 800 of conformality index vs. prescription dose. Homogeneity may be expressed in terms of a homogeneity index (HI), which is the ratio of the maximum dose to the prescription dose.

Figure 13:
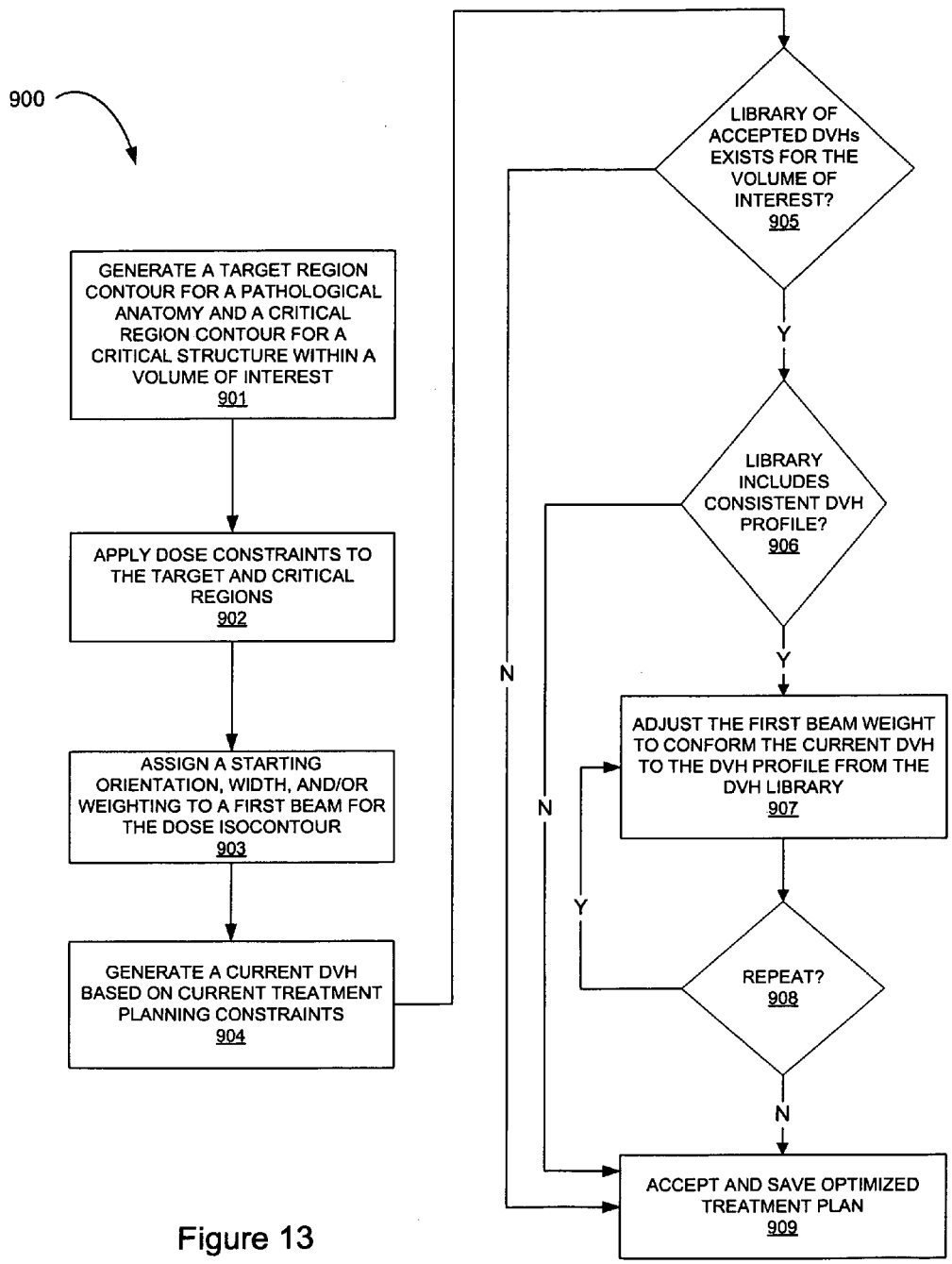
FIG. 13 is a flowchart illustrating one embodiment of a method of inverse treatment planning.

FIG. 13 is a flowchart 900 illustrating one embodiment of a method of inverse treatment planning. Flowchart 900 is described with respect to an example of delivering a radiation dose to a pathological anatomy near a critical structure, but the method of the present invention is not so limited and may be applied to the delivery of radiation dose to any pathological anatomies in other anatomies of a patient. In one embodiment, anatomical data of the pathological anatomy is obtained by acquiring an anatomical image (e.g., CT) to form a three-dimensional view of the pathological anatomy and the surrounding tissue. An exemplary CT scan is the axial slice of a patient's prostate gland as shown above with respect to CT scan 300 of FIG. 5. The CT image displays the location and size of the pathological anatomy (e.g., 303) and its surrounding tissue, including critical structures (e.g., rectum 304).

In examining the anatomical image on a display screen, the operator can identify the target region (e.g., pathological anatomy, lesion, tumor) for radiation treatment, and the presence of any critical regions near the target region for consideration so that the critical regions receive as little radiation as possible. In step 901, the operator delineates the target and critical regions by contouring these regions on the display screen (e.g., contours for pathological anatomy 303 and rectum 304). The operator can now input one or more treatment planning constraints to maximize conformality and homogeneity. One type of treatment planning constraint is minimum dose for the target region and maximum dose for the critical region, step 902. Another type of treatment planning constraint relates to the radiation beams for use in the treatment. For example, a starting beam weight (e.g., weight_1 306), width, or orientation for all the beams that are to be used in the treatment are given assigned values, step 903. In alternative embodiments, the operator may input other types of treatment planning constraints.

Based on the current treatment planning constraints, the treatment planning software generates current dose isocontours (e.g., 312) and a current DVH for the target and critical regions (e.g., DVH 401), step 904. Based on the results from the current DVH and/or dose isocontours, the current treatment plan may require optimization. In one embodiment, the optimization process may involve referencing a library of accepted plans to determine whether the current treatment plan should generate a DVH with a particular value or profile. The treatment planning software determines whether a library of accepted plans exists for the VOI of the current treatment plan, step 905. In one embodiment, the library of accepted plans may be a collection of DVHs for target and critical regions. For example, if the current treatment plan involves a pathological anatomy located within the prostate gland and near the rectum, the treatment planning software would determine whether such a library of plans exists. If a library of accepted plans exists, the treatment planning software next determines whether the DVHs have a consistent profile, step 906. If there is no library of accepted plans or there is no consistency to the library plans, the current treatment plan is not optimized with DVH values from a plan library. The current treatment plan may be accepted and stored as is, or other optimization processed may be applied, step 909.

If there is a consistent profile or value to the library of DVHs (e.g., as shown in FIG. 8), the treatment planning software automatically attempts to modify one or more constraints to conform the current DVH to the plan library DVHs. In one embodiment, the first beam weight is adjusted, step 907. For example, one or more beam weights involved in the treatment plan may be adjusted according to the algorithm described above. After a beam weight is adjusted, a new current DVH is generated and compared to the plan library DVHs, in which case one or beam weights may be adjusted again to refine the current DVH, step 908. If the optimized DVH value or profile is acceptable, the new current treatment plan is accepted and saved, step 909.

In one embodiment, the treatment planning process may involve aspects of both forward and inverse planning techniques, thereby combining the strengths of forward and inverse planning techniques. For example, the operator can utilize isocentric beam geometries or a mixture of non-isocentric and isocentric beam geometries as part of forward planning and subsequently modify the topology of isodose contours directly during inverse planning using aspects of the optimization process described herein (e.g., the method described with respect to flowchart 900). The operator can control each beam for use in the treatment plan in terms of radiation emission point, a distance to the target region, an orientation, and a radiation dose weight. The treatment planning software can allow the operator to specify a set of beams (and associated paths, emission points, and dose weights) to be used as part of a forward planning process, and another set of beams to be used as part of inverse planning. The set of beams reserved for inverse planning may be optimized by referencing an accepted plan library as described herein, or alternatively, both sets of beams may be optimized.

Figure 14:
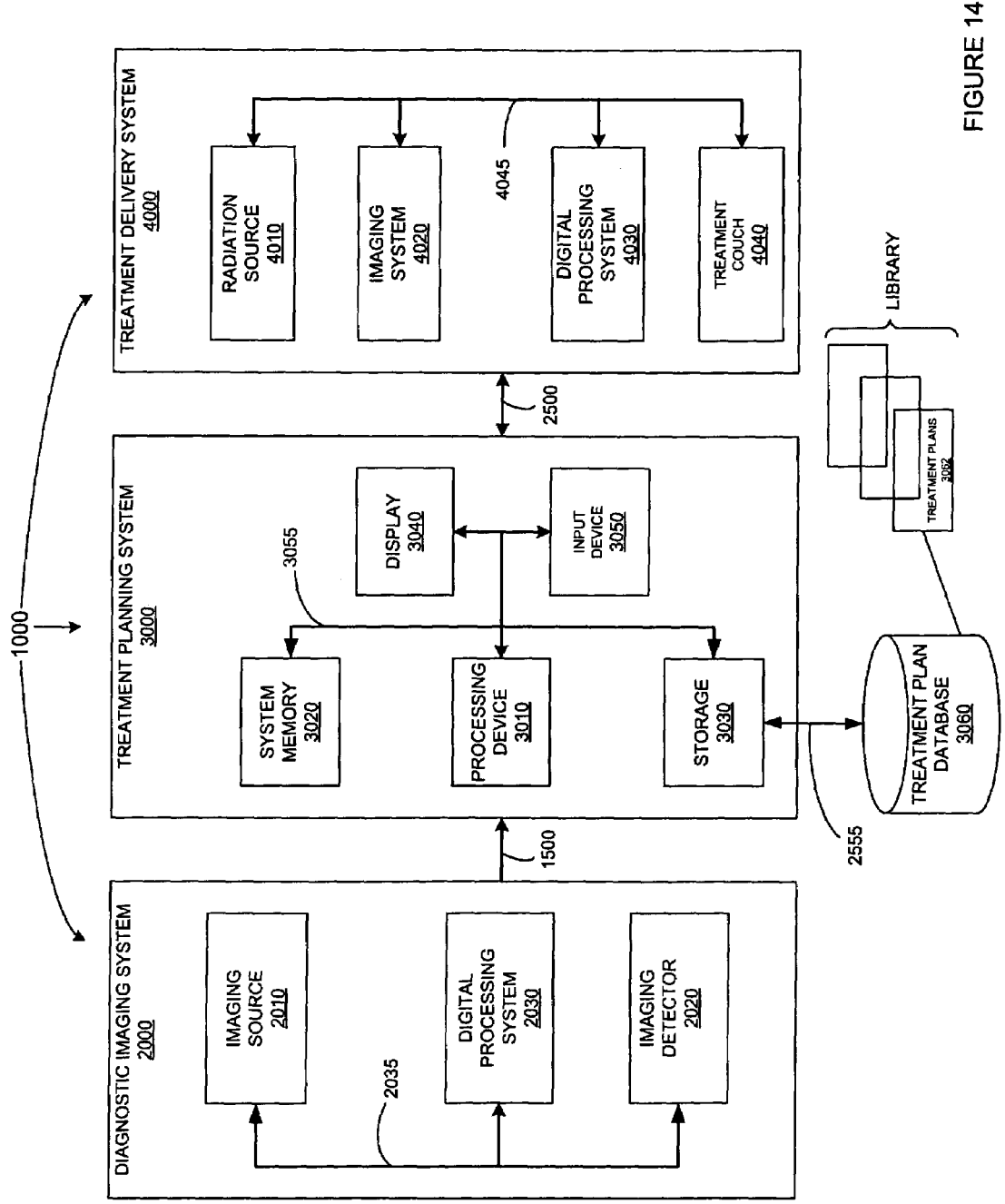
FIG. 14 illustrates one embodiment of systems that may be used to perform radiation treatment in which features of the present invention may be implemented.

FIG. 14 illustrates one embodiment of systems that may be used to perform radiation treatment in which features of the present invention may be implemented. As described below and illustrated in FIG. 14, system 1000 may include a diagnostic imaging system 2000, a treatment planning system 3000, and a treatment delivery system 4000.

Diagnostic imaging system 2000 may be any system capable of producing medical diagnostic images of a volume of interest (VOI) in a patient that may be used for subsequent medical diagnosis, treatment planning and/or treatment delivery. For example, diagnostic imaging system 2000 may be a computed tomography (CT) system, a magnetic resonance imaging (MRI) system, a positron emission tomography (PET) system, an ultrasound system or the like. For ease of discussion, diagnostic imaging system 2000 may be discussed below at times in relation to a CT x-ray imaging modality. However, other imaging modalities such as those above may also be used.

Diagnostic imaging system 2000 includes an imaging source 2010 to generate an imaging beam (e.g., x-rays, ultrasonic waves, radio frequency waves, etc.) and an imaging detector 2020 to detect and receive the beam generated by imaging source 2010, or a secondary beam or emission stimulated by the beam from the imaging source (e.g., in an MRI or PET scan). In one embodiment, diagnostic imaging system 2000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 2010 and the imaging detector 2020 are coupled to a digital processing system 2030 to control the imaging operation and process image data. Diagnostic imaging system 2000 includes a bus or other means 2035 for transferring data and commands among digital processing system 2030, imaging source 2010 and imaging detector 2020. Digital processing system 2030 may include one or more general-purpose processors (e.g., a microprocessor), special purpose processor such as a digital signal processor (DSP) or other type of device such as a controller or field programmable gate array (FPGA). Digital processing system 2030 may also include other components (not shown) such as memory, storage devices, network adapters and the like. Digital processing system 2030 may be configured to generate digital diagnostic images in a standard format, such as the DICOM (Digital Imaging and Communications in Medicine) format, for example. In other embodiments, digital processing system 2030 may generate other standard or non-standard digital image formats. Digital processing system 2030 may transmit diagnostic image files (e.g., the aforementioned DICOM formatted files) to treatment planning system 3000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 3000 includes a processing device 3010 to receive and process image data. Processing device 3010 may represent one or more general-purpose processors (e.g., a microprocessor), special purpose processor such as a digital signal processor (DSP) or other type of device such as a controller or field programmable gate array (FPGA). Processing device 3010 may be configured to execute instructions for performing treatment planning operations discussed herein, for example, optimizing the current treatment plan by comparing a present DVH with a DVH from an accepted plan library.

Treatment planning system 3000 may also include system memory 3020 that may include a random access memory (RAM), or other dynamic storage devices, coupled to processing device 3010 by bus 3055, for storing information and instructions to be executed by processing device 3010. System memory 3020 also may be used for storing temporary variables or other intermediate information during execution of instructions by processing device 3010. System memory 3020 may also include a read only memory (ROM) and/or other static storage device coupled to bus 3055 for storing static information and instructions for processing device 3010.

Treatment planning system 3000 may also include storage device 3030, representing one or more storage devices (e.g., a magnetic disk drive or optical disk drive) coupled to bus 3055 for storing information and instructions. Storage device 3030 may be used for storing instructions for performing the treatment planning steps discussed herein, such as the optimization algorithm and the accepted plan libraries. Storage device 3030 may also be a database (e.g., treatment plan database 3060) dedicated to storing accepted plan libraries and all the data associated with them. In an alternative embodiment, treatment plan database 3060 may be a separate storage device connected either internally or externally to storage device 3030 via link 2500, which may be a direct link, a LAN link or a WAN link. As shown, database 3060 may include one or more libraries of accepted treatment plans 3062. Treatment plan database 3060 may be, in one embodiment, an accumulation of treatment plans over a period of time or a collection of treatment plans from other databases. For example, treatment plan database 3060 includes plan libraries from multiple treatment centers (e.g., hospitals throughout the world) for use in the optimization process.

Processing device 3010 may also be coupled to a display device 3040, such as a cathode ray tube (CRT) or liquid crystal display (LCD), for displaying information (e.g., a 2-dimensional or 3-dimensional representation of the VOI) to the user. An input device 3050, such as a keyboard, may be coupled to processing device 3010 for communicating information and/or command selections to processing device 3010. One or more other user input devices (e.g., a mouse, a trackball or cursor direction keys) may also be used to communicate directional information, to select commands for processing device 3010 and to control cursor movements on display 3040.

It will be appreciated that treatment planning system 3000 represents only one example of a treatment planning system, which may have many different configurations and architectures, which may include more components or fewer components than treatment planning system 3000 and which may be employed with the present invention. For example, some systems often have multiple buses, such as a peripheral bus, a dedicated cache bus, etc. The treatment planning system 3000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 3000 may share its database (e.g., data stored in storage device 3030) with a treatment delivery system, such as treatment delivery system 4000, so that it may not be necessary to export from the treatment planning system prior to treatment delivery. Treatment planning system 3000 may be linked to treatment delivery system 4000 via a data link 2500, which may be a direct link, a LAN link or a WAN link as discussed above with respect to data link 1500. It should be noted that when data links 1500 and 2500 are implemented as LAN or WAN connections, any of diagnostic imaging system 2000, treatment planning system 3000 and/or treatment delivery system 4000 may be in decentralized locations such that the systems may be physically remote from each other. Alternatively, any of diagnostic imaging system 2000, treatment planning system 3000 and/or treatment delivery system 4000 may be integrated with each other in one or more systems.

Treatment delivery system 4000 includes a therapeutic and/or surgical radiation source 4010 to administer a prescribed radiation dose to a target volume in conformance with a treatment plan. Treatment delivery system 4000 may also include an imaging system 4020 to capture intra-treatment images of a patient volume (including the target volume) for registration or correlation with the diagnostic images described above in order to position the patient with respect to the radiation source. Treatment delivery system 4000 may also include a digital processing system 4030 to control radiation source 4010, imaging system 4020, and a patient support device such as a treatment couch 4040. Digital processing system 4030 may include one or more general-purpose processors (e.g., a microprocessor), special purpose processor such as a digital signal processor (DSP) or other type of device such as a controller or field programmable gate array (FPGA). Digital processing system 4030 may also include other components (not shown) such as memory, storage devices, network adapters and the like. Digital processing system 4030 may be coupled to radiation source 4010, imaging system 4020 and treatment couch 4040 by a bus 4045 or other type of control and communication interface.

Figure 15:
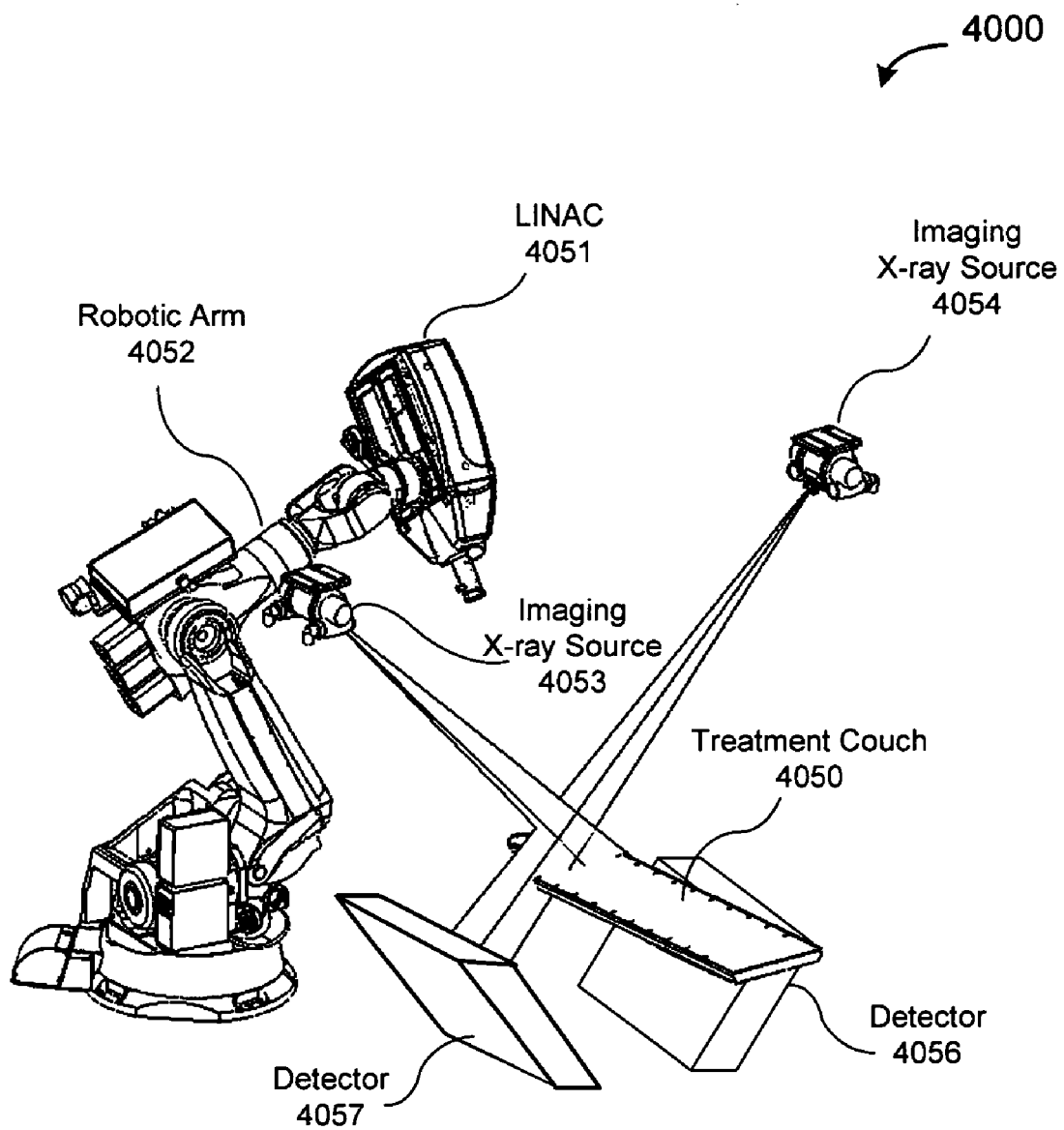
FIG. 15 illustrates one embodiment of a treatment delivery system.

In one embodiment, as illustrated in FIG. 15, treatment delivery system 4000 may be an image-guided, robotic-based radiation treatment system (e.g., for performing radiosurgery) such as the CyberKnife® system developed by Accuray Incorporated of California. In FIG. 15, radiation source 4010 may be represented by a linear accelerator (LINAC) 4051 mounted on the end of a robotic arm 4052 having multiple (e.g., 5 or more) degrees of freedom in order to position the LINAC 4051 to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target as illustrated in FIG. 6). Treatment can be delivered in either a single session (mono-fraction) or in a small number of sessions (hypo-fractionation) as determined during treatment planning. With treatment delivery system 4000, in one embodiment, radiation beams may be delivered according to the treatment plan without fixing the patient to a rigid, external frame to register the intra-operative position of the target volume with the position of the target volume during the pre-operative treatment planning phase.

In FIG. 15, imaging system 4020 may be represented by X-ray sources 4053 and 4054 and X-ray image detectors (imagers) 4056 and 4057. In one embodiment, for example, two x-ray sources 4053 and 4054 may be nominally aligned to project imaging x-ray beams through a patient from two different angular positions (e.g., separated by 90 degrees, 45 degrees, etc.) and aimed through the patient on treatment couch 4050 toward respective detectors 4056 and 4057. In another embodiment, a single large imager can be used that would be illuminated by each x-ray imaging source. Alternatively, other numbers and configurations of imaging sources and imagers may be used.

Digital processing system 4030 may implement algorithms to register images obtained from imaging system 4020 with pre-operative treatment planning images in order to align the patient on the treatment couch 4050 within the treatment delivery system 4000, and to precisely position the radiation source with respect to the target volume.

The treatment couch 4050 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 4050 may be a component of another mechanical mechanism, such as the Axum® treatment couch developed by Accuray Incorporated of California, or be another type of conventional treatment table known to those of ordinary skill in the art.

Alternatively, treatment delivery system 4000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met.

In other embodiments, yet another type of treatment delivery system 4000 may be used, for example, a stereotactic frame system such as the GammaKnife®, available from Elekta of Sweden. With such a system, the optimization algorithm (also referred to as a sphere packing algorithm) of the treatment plan determines the selection and dose weighting assigned to a group of beams forming isocenters in order to best meet provided dose constraints.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
    generating a current planning result guide for a volume of interest during a radiation treatment planning process, the current planning result guide based on a parameter for a treatment planning constraint; and
    adjusting automatically the treatment constraint to conform the current planning result guide with an accepted planning result guide from a plan library.

2. The method of claim 1, wherein the current and accepted planning result guides are a homogeneity index.

3. The method of claim 1, wherein the current and accepted planning result guides are a conformality index.

4. The method of claim 1, wherein the current and accepted planning result guides are a maximum dose to a region in the volume of interest.

5. The method of claim 1, wherein adjusting further comprises comparing the current planning result guide for a target region with the accepted planning result guide from the plan library corresponding to a volume of interest that includes the target region.

6. The method of claim 5, wherein adjusting further comprises comparing the current planning result guide for a critical region with the accepted
    planning result guide from the plan library corresponding to a volume of interest that includes the critical region.

7. The method of claim 1, wherein the parameter comprises a beam weight and adjusting further comprises modifying the beam weight.

8. The method of claim 7, wherein modifying further comprises at least one of incrementally increasing or incrementally decreasing the beam weight until the current planning result guide closely matches the accepted planning result guide.

9. The method of claim 7, wherein the current and accepted planning result guides are a dose volume histogram.

10. The method of claim 1, wherein the parameter comprises a beam orientation and adjusting further comprises modifying the beam orientation.

11. The method of claim 10, wherein the current and accepted planning result guides are a dose volume histogram.

12. A method, comprising:
    generating a first contour around a pathological anatomy, within a volume of interest, to identify a target region and a second contour around a critical structure to identify a critical region;
    assigning a first beam weight associated with a first radiation beam directed towards the target region;
    generating a current planning result guide associated with the critical region based on the first beam weight; and
    adjusting automatically the first beam weight to conform the current planning result guide to an accepted planning result guide from a plan library.

13. The method of claim 12, wherein adjusting further comprises deriving the accepted planning result guide from the plan library from a plurality of accepted plans.

14. The method of claim 13, wherein adjusting further comprises calculating a deviation between the current planning result guide and the accepted planning result guide from the plan library.

15. The method of claim 14, wherein adjusting further comprises modifying the first beam weight to a second beam weight.

16. The method of claim 15, wherein modifying further comprises at least one of incrementally increasing or incrementally decreasing the first beam weight to the second beam weight until the current planning result guide closely matches the accepted planning result guide from the plan library.

17. The method of claim 12, wherein the current and accepted planning result guides are a homogeneity index.

18. The method of claim 12, wherein the current and accepted planning result guides are a conformality index.

19. The method of claim 12, wherein the current and accepted planning result guides are a maximum dose to a region in the volume of interest.

* * * * *